United States Patent [19]

Heinz et al.

[11] Patent Number: 5,169,982

[45] Date of Patent: Dec. 8, 1992

[54] PROCESS FOR SEPARATING IODINE AND ITS COMPOUNDS FROM THE PRODUCTS OBTAINED ON SUBJECTING DIMETHYLETHER, METHYL ACETATE OR METHANOL TO CARBONYLATION

[75] Inventors: Erpenbach Heinz, Cologne; Klaus Gehrmann; Peter Hörstermann, both of Erftstadt, all of Fed. Rep. of Germany

[73] Assignee: Hoechst Aktiengesellschaft, Frankfurt am Main, Fed. Rep. of Germany

[21] Appl. No.: 907,866

[22] Filed: Sep. 16, 1986

[30] Foreign Application Priority Data

Sep. 30, 1985 [DE] Fed. Rep. of Germany ....... 3534815
Apr. 14, 1986 [DE] Fed. Rep. of Germany ....... 3612504

[51] Int. Cl.$^5$ ..................... C07C 67/36; C07C 51/10; C07C 51/14; C07C 51/12
[52] U.S. Cl. .................... 560/232; 560/248; 562/517; 562/519; 562/608; 562/898
[58] Field of Search ............... 560/232, 248; 562/517, 562/519, 608, 890, 898; 260/546, 549

[56] References Cited

FOREIGN PATENT DOCUMENTS 0013551 7/1980 European Pat. Off. ............ 560/248
2112394 7/1983 United Kingdom ................ 562/608

OTHER PUBLICATIONS

House, Modern Synthetic Reactions, Second Edition, The Benjamin/Cummings Publishing Co., pp. 292-293.
Condensed Chemical Dictionary, 6th Ed. (ed. Rose et al), Reinhold Pub. Co., New York, N.Y., 1961, pp. 864-865.

Primary Examiner—Jose G. Dees
Assistant Examiner—Joseph M. Conrad, III

[57] ABSTRACT

Iodine and its compounds are separated from the carbonylation products acetic acid, acetic anhydride or ethylidene diacetate obtained on subjecting dimethylether, methyl acetate or methanol to a carbonylation reaction in the presence of an iodine-containing catalyst. The quantity of total iodine contaminating the carbonylation products is reduced to less than 20 ppb iodine by treating the products at 20°-200° C. with peracetic acid, diacetyl peroxide or a compound yielding these two agents under the reaction conditions, and separating them distillatively.

9 Claims, No Drawings

PROCESS FOR SEPARATING IODINE AND ITS COMPOUNDS FROM THE PRODUCTS OBTAINED ON SUBJECTING DIMETHYLETHER, METHYL ACETATE OR METHANOL TO CARBONYLATION

This invention relates to a process for separating iodine and its compounds from the carbonylation products acetic acid and/or acetic anhydride and/or ethylidene diacetate obtained on subjecting dimethylether and/or methyl acetate and/or methanol to a carbonylation reaction in the presence of an iodine-containing catalyst.

The reaction mixtures obtained in carbonylation reactions of the kind described e.g. in German Specification DE-A-28 36 084, are customarily worked up distillatively. To this end, the non-volatile catalyst constituents are separated from the volatile constituents of the reaction mixture, in a first separating stage. Next, the low-boilers methyl iodide and unreacted methyl acetate, dimethylether and methanol, if any, forming part of the volatile constituents are distilled off overhead a low boiler column. Following this, acetic acid, acetic anhydride and ethylidene diacetate, if any, are separated overhead in the sequential order indicated in three further columns downstream of the low boiler column.

The carbonylation products so made are contaminated with iodine compounds the low concentration in the magnitude of ppm of which makes it difficult for them to be specified so that they find limited uses only in noble metal-catalyzed industrial processes.

German Specification DE-B-21 04 828 describes a process for removing minor quantities of halide contaminants from acetic acid preferably made by reacting an alcohol or olefin with carbon monoxide in the presence of a catalyst system comprising a noble metal constituent and halide constituent, by treating the acid with potassium permanganate, sodium permanganate, potassium dichromate, sodium dichromate, chromium trioxide, chromium potassium oxalate, potassium chlorochromate, potassium chlorate and/or potassium chromate at 16°–200° C. More particularly, acetic acid containing less than 500 ppb halide, especially iodide, is brought into contact, prior to or during distillation, with one of the metal compounds aforesaid which are used in a quantity of up to 1.0 wgt %, based on acetic acid, and 90–98% halide compound is separated in this way. This process is however considerably less suitable for purifying carbonylation products containing acetic anhydride; the reason resides in the fact that the oxidants also undergo reaction with acetic anhydride and then can no longer fix the iodide.

German Specification DE-A-22 56 510 discloses a process for removing very minor quantities of iodide from acetic acid in a system comprised of two distilling columns; depending on its initial iodine content, the feed acid can be freed from iodine-containing compounds to a residual content of less than 40 ppb to less than 5 ppb by admixing it with an oxide, hydroxide, carbonate, bicarbonate and salt of a weak organic acid of an alkali metal and alkaline earth metal or with a mixture of an alkali metal or alkaline earth metal compound and hypophosphorous acid. In this process, the salts of the alkali and alkaline earth metals as well as the hypophosphorous acid are used in the form of an aqueous solution. As a result, the decontaminating method just described should conveniently not be used for effecting the separation of contaminating iodine compounds from acetic anhydride, as the anhydride undergoes saponification.

German Specification DE-A-29 01 359 relates to a process for removing iodine from organic compounds, especially from mixtures obtained by an oxidizing acylation of olefines with an iodine-containing catalyst, e.g. carboxylic acid esters of ethylene or propylene glycol, wherein the iodine-containing organic compounds are treated at 50°–200° C. with an oxidant and the reaction mixture is simultaneously or subsequently brought into contact with an adsorbent for iodine. The preferred oxidants include oxygen and hydrogen peroxide and the adsorbent preferably is active carbon. The oxidant used in the working Examples of that Specification is hydrogen peroxide of 20% strength. 92.4–99.5% of the iodine is removed, but the residual iodine content is still as high as 40 ppm and definitely fails to satisfy purity requirements. In this process, too, it is a disadvantage that water again gets into the system by the use of hydrogen peroxide.

German Specification DE-A-31 07 731 is directed to a process for separating organic iodine compounds from carbonylation products of methanol, methyl acetate and dimethylether by liquid phase extraction using a nonaromatic hydrocarbon. As results from the working Examples in that Specification, the iodine content can be reduced to at most 100 ppb iodine. Apart from these iodine values which are too high, the process is rendered considerably more expensive by the need to subject the extractant to an additional distilling operation.

German Specification DE-A-29 40 751 teaches separating iodine compound contaminants from carbonylation products of methyl acetate by subjecting them to treatment with cesium acetate, potassium acetate and/or sodium acetate while obtaining the corresponding alkali metal iodides. The methyl iodide separation to only 2 ppm does not comply with the purity specifications demanded of a purified carbonylation product for work-up. It is incidentally not possible by gas-chromatographic analysis, based on methyl iodide, accurately to determine the total iodine contained in the carbonylation product so that it is really difficult to make a definite statement relative to the iodine separation actually achieved.

The present invention now provides a process permitting alkyl and aryl iodides or other easily distillable iodine-containing compounds to be removed and also iodine in whatever fixed or elemental form to be almost quantitatively separated from the feed product to be purified. Exemplary representatives of removable iodine compounds are butyl iodide, iodoacetone, acetyl iodide, hydrogen iodide and also substituted ammonium and phosphonium iodides.

The process of this invention comprises more particularly reducing the quantity of total iodine contaminating the carbonylation products to less than 20 ppb iodine by treating the products at 20°–200° C. with peracetic acid, diacetyl peroxide or a compound yielding these agents under the reaction conditions, and separating them distillatively.

Further preferred and optional features of the process of this invention provide:
a) for carbonylation products containing less than 100 ppm total iodine to be used as feed material;
b) for the carbonylation products to be treated at 100°–140° C. over a period of 0.5–120 minutes;

c) for the carbonylation products treated with peracetic acid, diacetyl peroxide or compound yielding these agents under the reaction conditions to be subjected to fractional distillation.

The iodine compounds or elemental iodine very difficult to separate distillatively which are still contained in the carbonylation products already freed from catalyst and low boiler fractions are unexpectedly converted to distillatively easily separable iodine compounds by subjecting them to the treatment with peracetic acid in accordance with this invention so that carbonylation products practically free from iodine are obtained after distillation without the need to use an absorbent.

The treatment with peracetic acid has a particular advantage associated with it, namely that the acid undergoes reaction with the iodine compounds in the presence of acetic anhydride to give acetic acid, the concentration of the acetic acid invariably present in the mixture of the carbonylation products being increased insignificantly only.

The peracetic acid should suitably be used in at least stoichiometric proportions, based on the total iodine content in the carbonylation products, but it is good practice to make sure that the mixture of carbonylation products to be subjected to further distillative work-up no longer contains unreacted peracetic acid.

EXAMPLE 1

1000 g of a carbonylation product mixture containing 80 mass % acetic anhydride, 20 mass % acetic acid and 800 ppb iodine in the form of not accurately determined iodine compounds was admixed with 30 g of a 10% anhydrous peracetic acid solution in glacial acetic acid and the whole was heated for 60 minutes to 120° C. Next, the mixture was fractionated and pure acetic acid and pure acetic anhydride containing less than 10 ppb iodine were obtained.

EXAMPLE 2 (comparative Example)

Example 1 was repeated save that the addition of the peracetic acid solution was omitted. Acetic acid containing 2800 ppb iodine and acetic anhydride containing 300 ppb iodine were obtained by fractionation.

EXAMPLE 3

1000 g of a carbonylation product mixture containing 90 mass % acetic anhydride, 10 mass % acetic acid and 1200 ppb iodine in the form of not accurately determined iodine compounds was admixed with 20 g of a 10% anhydrous peracetic acid solution in glacial acetic acid and the whole was heated for 15 minutes to 132° C. Pure acetic acid and pure acetic anhydride containing less than 10 ppb iodine were obtained by fractionation.

EXAMPLE 4 (COMPARATIVE EXAMPLE)

Example 3 was repeated save that the addition of the peracetic acid solution was omitted. Acetic acid containing 7000 ppb iodine and acetic anhydride containing 400 ppb iodine were obtained by fractionation.

EXAMPLE 5

20 g of a 10% anhydrous peracetic acid solution in glacial acetic acid was continuously metered over a period of 15 minutes at 132° C. into 1000 g of a carbonylation product mixture containing 80 mass % acetic anhydride, 20 mass % acetic acid and 1100 ppb iodine in the form of not accurately determined iodine compounds. Acetic acid and acetic anhydride containing less than 10 ppb iodine were obtained by fractionation.

EXAMPLE 6

The apparatus was a continuously operated pilot plant for the production of acetic anhydride by subjecting dimethylether and methyl acetate to carbonylation. 100 parts of a product stream containing 80 mass % acetic anhydride, 20 mass % acetic acid and 600 ppb iodine, obtained after separation of the noble metal catalyst and low-boiling methyl iodide and unreacted methyl acetate were placed in a tube reactor and continuously admixed therein at 138° C. over a mean period of 30 minutes with 3 parts of a 10% anhydrous solution of peracetic acid in glacial acetic acid. Acetic acid and acetic anhydride containing less than 10 ppb iodine were obtained by fractionation.

EXAMPLE 7

Example 6 was repeated save that the peracetic acid solution was metered at 138° C. directly into the still of the low boiler column in which the methyl iodide and unreacted methyl acetate were quantitatively separated overhead; this corresponded to a mean residence time of 20 minutes. The still product was subsequently fractionated and acetic acid and acetic anhydride containing less than 10 ppb iodine were obtained.

EXAMPLE 8 (COMPARATIVE EXAMPLE)

Example 7 was repeated but without addition of peracetic acid solution to the still product of the low boiler column. The product was fractionated and acetic acid containing 2400 ppb iodine and acetic anhydride containing 150 ppb iodine were obtained.

We claim:

1. A process for separating iodine and its compounds from the carbonylation products acetic acid, acetic anhydride or ethylidene diacetate obtained on subjecting dimethylether, methyl acetate or methanol to a carbonylation reaction in the presence of an iodine-containing catalyst which comprises reducing the quantity of total iodine contaminating the carbonylation products to less than 20 ppb in a single stage by admixing peracetic acid or diacetyl peroxide with these carbonylation products at 20°-200° C. and separating the resulting mixture by distillation.

2. A process as claimed in claim 1, wherein carbonylation products containing less than 100 ppm total iodine are used as feed material.

3. A process as claimed in claim 1, wherein the carbonylation products are treated at 100°-140° C. over a period of 0.5-120 minutes.

4. A process as claimed in claim 1, wherein the carbonylation products, after admixture with peracetic acid or diacetyl peroxide are subjected to fractional distillation.

5. A process as claimed in claim 1, wherein the carbonylation products are admixed with peracetic acid dissolved in glacial acetic acid.

6. A process as claimed in claim 1, wherein the carbonylation products are admixed with anhydrous peracetic acid.

7. A process as claimed in claim 1, wherein the contaminated carbonylation products are essentially freed of iodine content without the use of an adsorbent.

8. A process for separating iodine and its compounds from the carbonylation products acetic acid, acetic anhydride or ethylidene diacetate obtained on subjecting dimethylether, methyl acetate or methanol to a carbonylation reaction in the presence of an iodine-containing catalyst which comprises reducing the quantity of total iodine contaminating the carbonylation products to less than 20 ppb in a single stage by admixing anhydrous peracetic acid with the carbonylation products at 20°–200° C. and separating the resulting mixture by distillation.

9. A process as claimed in claim 8, wherein the contaminated carbonylation products are essentially freed of iodine content without the use of an adsorbent.

* * * * *